United States Patent [19]

Yabe

[11] Patent Number: 4,641,635

[45] Date of Patent: Feb. 10, 1987

[54] ENDOSCOPE APPARATUS

[75] Inventor: Hisao Yabe, Tokyo, Japan

[73] Assignee: Olympus Optical Co., Ltd., Tokyo, Japan

[21] Appl. No.: 763,978

[22] Filed: Aug. 9, 1985

[30] Foreign Application Priority Data

Aug. 15, 1984 [JP] Japan .................................. 59-170170
Aug. 15, 1984 [JP] Japan .................................. 59-170173

[51] Int. Cl.$^4$ ............................ A61B 1/04; A61B 1/06
[52] U.S. Cl. ............................................ 128/6; 358/98
[58] Field of Search ............................ 128/4, 6; 358/98

[56] References Cited

U.S. PATENT DOCUMENTS 3,417,745  12/1968  Sheldon ................................ 128/6
3,818,902  6/1974   Kinoshita et al. ...................... 128/6
4,519,391  5/1985   Murakoshi ............................. 128/4 X Primary Examiner—William H. Grieb

[57] ABSTRACT

An endoscope has an insertion section extended from an operation section. An observation window and an illumination window are formed in the distal end of the insertion section. The observation window is positioned nearer the distal end of the insertion section than the illumination window. A light guide extends from the illumination window through the insertion section and guides light emitted from a light source to emit the light from the illumination window. An objective lens system is arranged in the insertion section and optically connected to the observation window. An optical image of light, incident on the system through the observation window, is formed by the system. A solid-state image sensor is arranged in the insertion section and positioned nearer the distal end of the insertion section than the end of the light guide at the illumination window side. The sensor converts the optical image to an electrical signal and transmits it to a control unit.

11 Claims, 13 Drawing Figures

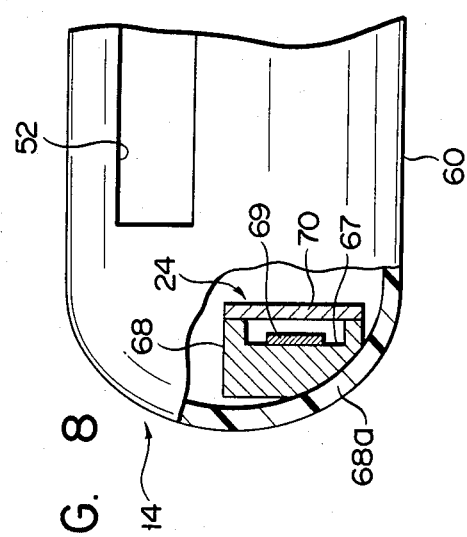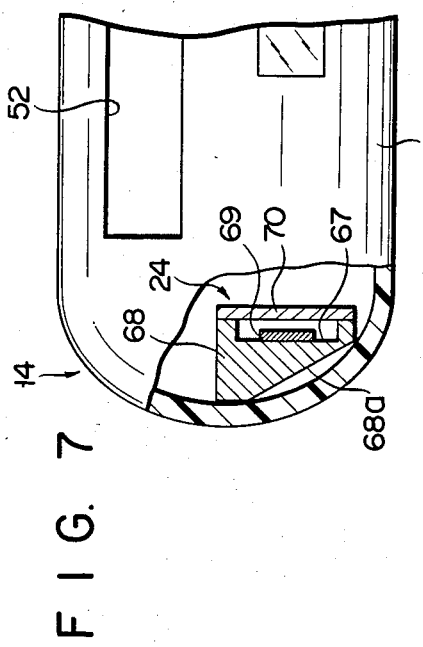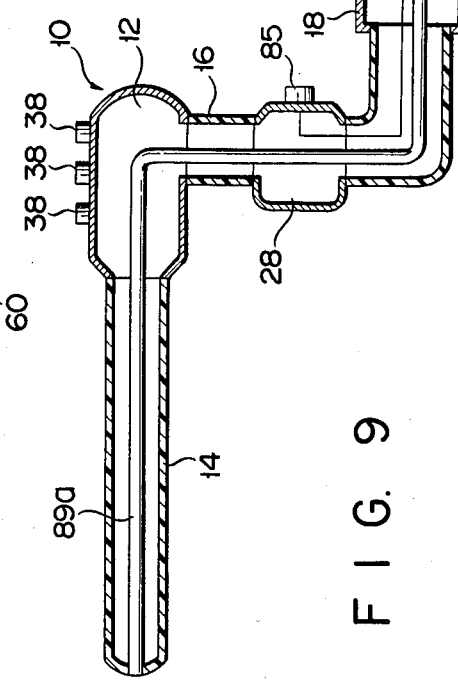

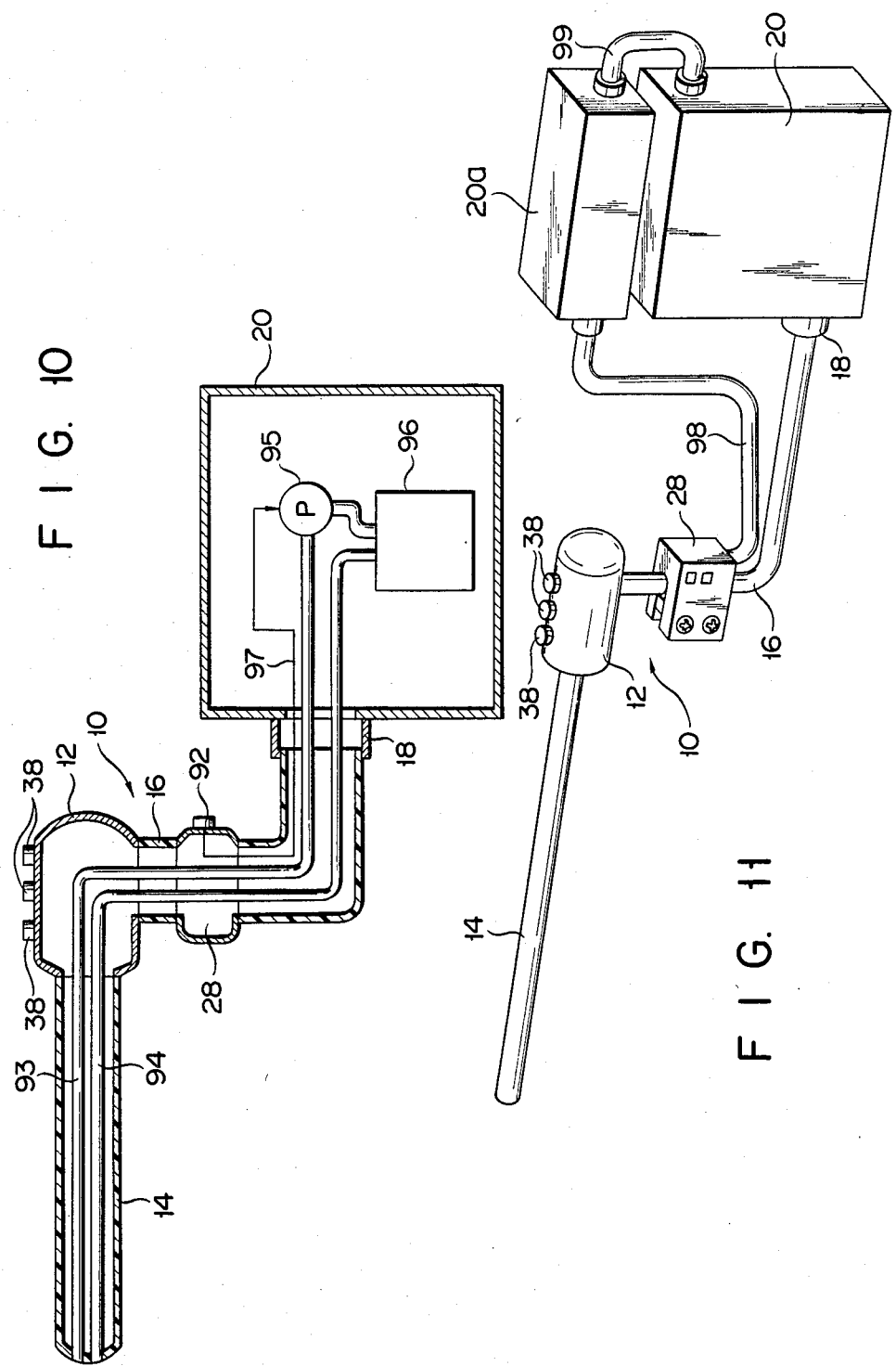

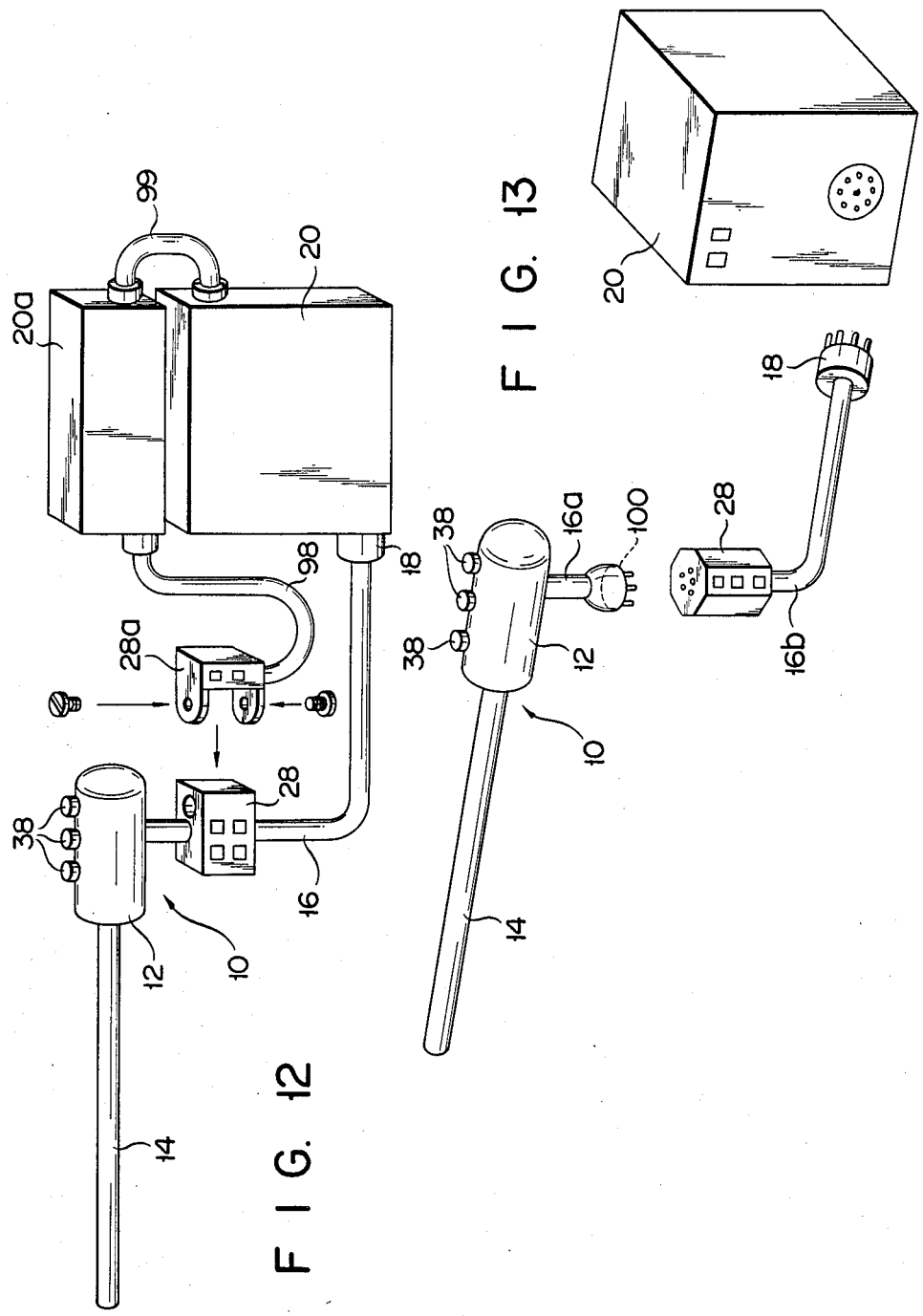

ENDOSCOPE APPARATUS

BACKGROUND OF THE INVENTION

The present invention relates to an endoscope apparatus and, more particularly, to an endoscope apparatus for observing a body cavity by using a solid-state image sensor.

A conventional endoscope apparatus having a solid-state image sensor inside a distal end of an endoscope is known. In an apparatus of this type, an optical image formed by an objective lens system provided inside the distal end of an insertion section is converted to an electrical signal by an image sensor. The electrical signal is then signal-processed and displayed as an image on a monitor. With such an endoscope apparatus, the optical image can be stably transmitted compared to the case of an endoscope using an image guide consisting of a bundle of optical fibers. Moreover, the image can be simultaneously observed by a group of people.

Conventionally, an observation window and an illumination window are provided at a distal end portion of the insertion section of the endoscope, and the illumination window is formed at the leading end side of the observation window in the insertion section. An objective lens system is connected to the observation window through a prism and a solid-state image sensor is provided to oppose the objective lens system. An end of a light guide consisting of a bundle of optical fibers opposes the illumination window and the light guide extends to a proximal end of the insertion section therethrough. In the endoscope of this structure, the image sensor and the light guide are located on an identical cross section of the insertion section, i.e., the image sensor and the light guide are aligned along the radial direction of the insertion section. Therefore, the outer diameter of the insertion section is determined by the sum of the height of the image sensor and the diameter of the light guide. As a result, it is difficult to decrease the diameter of the distal end of the insertion section, and the patient experiences severe discomfort when the insertion section is inserted into a body cavity.

SUMMARY OF THE INVENTION

The present invention has been made in consideration of the above circumstances and has as its object to provide an endoscope apparatus wherein the diameter of a distal end of an insertion section can be decreased even when a solid-state image sensor is provided.

In order to obtain the above-mentioned object, an endoscope apparatus according to the present invention comprises: a control unit having a light source; and an endoscope, the endoscope including an operation section, an elongated insertion section extending from the operation section and having an observation window and an illumination window provided at a distal end thereof, the observation window being positioned at the leading end side of the illumination window of the insertion section, a universal cord extending from the operation section and detachably connected to the control unit, a light guide extending from the illumination window through the insertion section, operation section and the universal cord for guiding light emitted from the light source and emitting the light externally from the illumination window, an objective lens system arranged in the insertion section and optically connected to the observation window for forming an optical image of light incident thereon through the observation window, and a solid-state image sensor provided at the leading end side of the illumination window of the light guide in the insertion section and optically connected to the objective lens system for converting the optical image formed by the objective lens system to an electrical signal and transmitting the electrical signal to the control unit.

BRIEF DESCRIPTION OF THE DRAWINGS

FIGS. 1 to 4 show an endoscope apparatus according to a first embodiment of the present invention, in which FIG. 1 is a sectional view for schematically showing an overall configuration of the apparatus, FIG. 2 is an enlarged side view of a distal end of an insertion section, FIG. 3 is a sectional view taken along the line III—III of FIG. 2, and FIG. 4 is a sectional view of an image sensor;

FIGS. 7 and 8 are sectional views of distal ends of insertion sections of endoscope apparatuses according to different modifications of the present invention; and FIGS. 9 to 13 are sectional views for schematically showing endoscope apparatuses according to fourth to eighth embodiments of the present invention.

DETAILED DESCRIPTION OF THE PREFERRED EMBODIMENTS

Preferred embodiments of the present invention will now be described with reference to the accompanying drawings.

Figure 1:
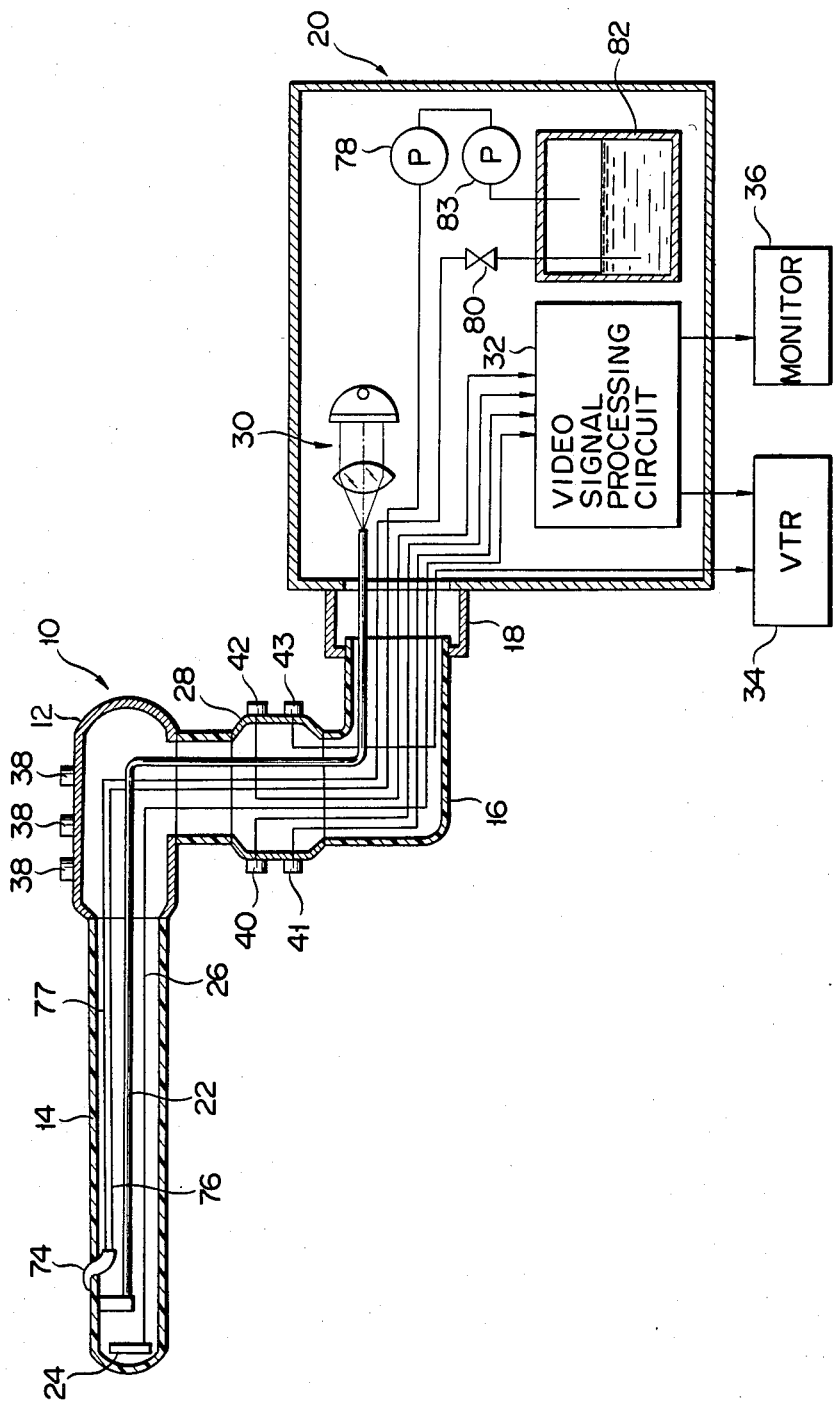

Referring to FIG. 1, an endoscope apparatus has a side view type endoscope 10. The endoscope 10 has an operation section 12, an elongated flexible insertion section 14 extending from the operation section 12, and a universal cord 16 extending from the operation section 12. A connector 18 is attached to the extended end of the universal cord 16. The connector 18 is detachably connected to an endoscope control unit 20. The endoscope 10 has a light guide 22 extending from the extended end of the insertion section 14 to the connector 18. A solid-state image sensor 24 is arranged inside the distal end of the insertion section 14. A lead wire 26 extends from the image sensor 24 to the connector 18. A nozzle 74 is provided at the distal end of the insertion section 14. An air supply pipe 76 and a liquid supply pipe 77 extend from the nozzle 74 to the connector 18 through the endoscope 10. A sub-operation section 28 is provided midway along the universal cord 16.

A light source 30 and a video signal processing circuit 32 are arranged in the control unit 20. A VTR 34 and a monitor 36 are connected to the video signal processing circuit 32. When the connector 18 is connected to the control unit 20, the light guide 22 is optically connected to the light source 30 and the lead wire 26 is electrically connected to the circuit 32. The light guide 22 guides light emitted from the light source 30 to the distal end of the insertion section 14. The image sensor 24 converts an optical image of an object to an electrical signal and supplies the electrical signal to the circuit 32 through the lead wire 26.

An air supply pump 78 and a liquid supply pump 83 for air/liquid supply, a valve 80 and a liquid tank 82 are arranged in the control unit 20.

Operation switches 38 for air/liquid supply and suction which are used very frequently are arranged at the operation section 12. Operation switches which are used less frequently such as an automatic gain control up switch 40 and down switch 41 for controlling brightness of the image, a freeze switch 42 for stopping the image and a pause switch 43 for temporarily stopping the image on the VTR 34 are provided at the sub-operation section 28. When the connector 18 is connected to the control unit 20, the pause switch 43 and the remaining switches 40, 41 and 42 are electrically connected to the VTR 34 and the circuit 32, respectively.

The structure of the distal end of the insertion section 14 will now be described in detail.

Figure 2:
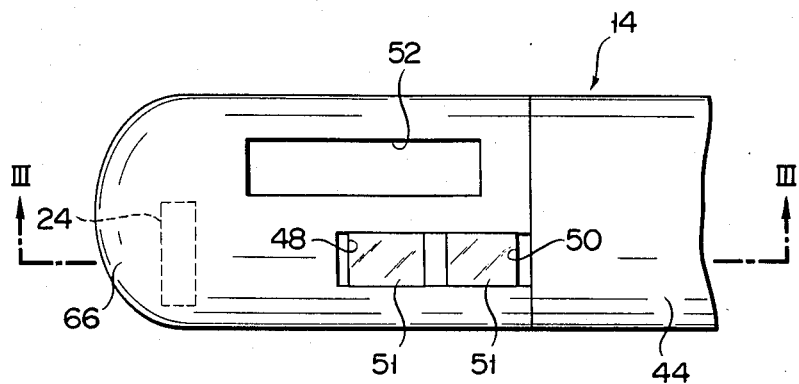
Figure 3:
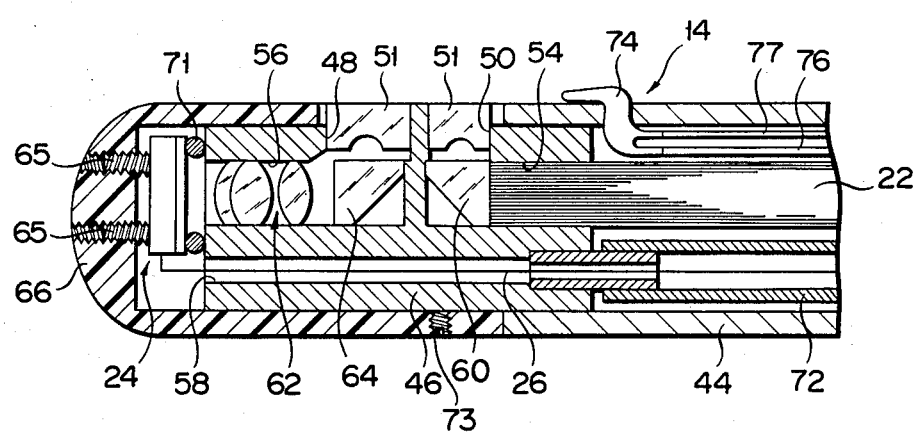

Referring to FIGS. 2 and 3, the insertion section 14 has a flexible outer tube 44 and a support 46 fitted in the distal end thereof. The support 46 is cylindrical and made of a hard material such as a metal. An illumination window 50 and an observation window 48 are formed in the outer surface of the support 46 to be axially spaced from each other. The observation window 48 is positioned nearer the distal end of the insertion section 14 than the illumination window 50. Cover glasses 51 are fitted in the windows 48 and 50. A forceps outlet 52 is formed in the support 46 on the side of the windows 48 and 50 and communicates with a forceps channel (not shown) extending through the section 14. A first mounting hole 54 communicating with the window 50 and a second mounting hole 56 communicating with the window 48 are formed in the support 46. The holes 54 and 56 are formed substantially coaxially and extend along the axial direction of the support 46. A through hole 58 is formed to extend through the support 46 along the axial direction thereof.

The distal end of the light guide 22 is inserted and fixed in the hole 54. A first prism 60 is arranged in the first hole 54. An end face of the prism 60 opposes the window 50, and the other face opposes the distal end face of the light guide 22. An objective lens system 62 including a plurality of lenses is arranged in the second hole 56 such that the optical axis thereof coincides with the axis of the hole 56. A second prism 64 is arranged in the second hole 56 such that an end face thereof opposes the window 48 and the other end face thereof opposes the objective lens system 62.

Figure 4:
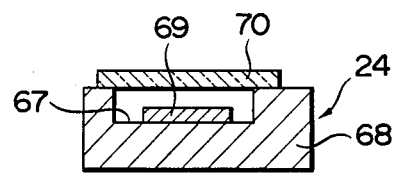

A cylindrical cap 66 with a bottom and made of, e.g., a synthetic resin, is fitted around the support 46. The image sensor 24 is arranged between the bottom of the cap 66 and the distal end face of the support 46. The image sensor 24 has a package 68 including a circular recess 67, a semiconductor chip 69 fixed to the bottom of the recess 67 and a transparent cover 70 fixed to the package 68 and closing the recess 67, as shown in FIG. 4. The image sensor 24 is arranged such that the chip 69 opposes the lens system 62 and the center of the chip 69 is positioned on the optical axis of the lens system 62. The image sensor 24 is urged by a plurality of, e.g., four, adjusting screws 65 screwed from the distal end of the cap 66 against the distal end face of the support 46 and abuts against it through an elastic O-ring 71. Focusing and inclination adjustment of the image sensor 24 can be performed by the adjusting screws 65. The cap 66 is fitted to be slidable along the axial direction of the support 46, and fixed to the support by a screw 73. Thus, focusing adjustment of the image sensor 24 can be also performed by sliding the cap 66. The lead wire 26 extends from the image sensor 24 to the connector 18 of the endoscope through the through hole 58 in the support 46 and a tube 72 connected to the through hole 58.

The nozzle 74 is attached on the outer surface of the distal end of the insertion section 14 and positioned at a position to the rear of the window 50. When the connector 18 is connected to the control unit 20, the air supply pipe 76 communicates with the pump 78, and the liquid supply pipe 77 communicates with the pump 83 through the valve 80 and the tank 82.

The operation of the endoscope apparatus having the above-mentioned structure will now be described. First, the insertion section 14 is inserted in a body cavity while the connector 18 of the endoscope 10 is connected to the control unit 20. When the light source 30 is turned on, light emitted from the light source 30 is guided to the distal end of the section 14 through the light guide 22 and is irradiated onto an object through the first prism 60 and the window 50. The optical image of the object is incident on the lens system 62 through the window 48 and the second prism 64 and is formed onto the semiconductor chip 69 of the image sensor 24 by the lens system 62. The image sensor 24 converts the optical image to an electrical signal. The electrical signal is supplied to the circuit 32 through the lead wire 26. The circuit 32 processes the electrical signal and outputs the processed signal to the VTR 34 and the monitor 36. Then, the image of the object is displayed on the monitor 36 and recorded by the VTR 34.

When the pumps 78 and 83 are operated and the valve 80 is opened, air is supplied to the pipe 76. Simultaneously, the liquid in the tank 82 is pressurized and supplied to the pipe 77. Then, a fluid mixture of air and liquid is sprayed to the windows 50 and 48 so that the windows are cleaned.

The endoscope apparatus having the above-mentioned structure has advantages as follows.

The image sensor 24 is arranged in the distal end side of the insertion section 14 and positioned nearer the distal end of the section 14 than the distal end of the light guide 22. Thus, the image sensor 24 and the light guide 22 do not overlap along the radial direction of the insertion section 14 so that the diameter of the distal end of the insertion section 14 can be decreased. The objective lens system 62 is arranged along the axial direction of the support 46, i.e., along the axial direction of the insertion section 14. Therefore, the distal end of the insertion section 14 can be narrowed compared with the case wherein a lens system is arranged along the radial direction of an insertion section.

The endoscope comprises the sub-operation section 28 formed midway along the universal cord 16. The operation switches 40 to 43 which are used less frequently are provided at the section 28. Therefore, only the operation switches 38 which are used frequently need be arranged in the operation section 12. Then, the number of the operation switches provided at the section 12 is not increased even though the endoscope has a variety of functions, thereby improving operability of the operation switches and decreasing the size of the operation section 12. An operator can operate the operation switches 40 to 43 on the sub-operation section 28 as he operates the endoscope 10. Therefore, the operator need not change his position unlike in the case where the operation switches are provided only at the control unit 20, thereby improving operability.

When the section 28 is provided at the universal cord 16, it can be washed and sterilized together with the endoscope 10. Even if the operation switches provided at the section 28 are operated, hygiene will not be impaired.

The present invention is not limited to the abovementioned embodiment and various modifications may be made within the scope of the present invention.

Figure 5:
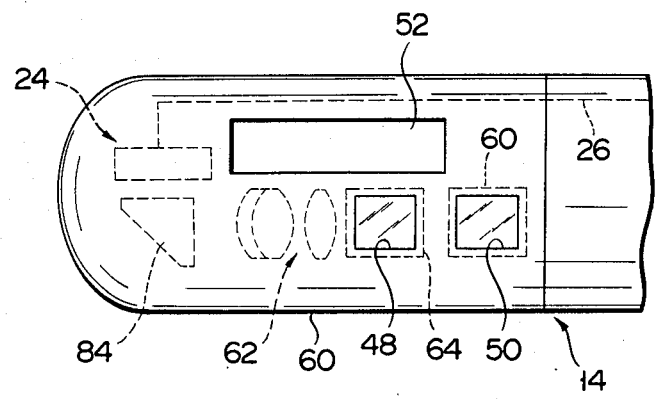
FIG. 5 is an enlarged side view of a distal end of an insertion section of an endoscope apparatus according to a second embodiment of the present invention.

FIG. 5 shows a second embodiment of the present invention. Referring to FIG. 5, a solid-state image sensor 24 is arranged along the axial direction of an insertion section 14. In other words, a third prism 84 is arranged on an emitting side of an objective lens system 62 such that an end face thereof opposes the lens system. The image sensor 24 opposes the other end face of the prism 84. An optical image focused by the lens system 62 is deflected by the prism 84 along the radial direction of the section 14, and becomes incident on the image sensor 24.

According to the second embodiment having the above-mentioned configuration, a space in the distal end of the section 14 at the leading side of a forceps outlet 52 can be effectively used, in addition to the effect of the first embodiment described above.

Figure 6:
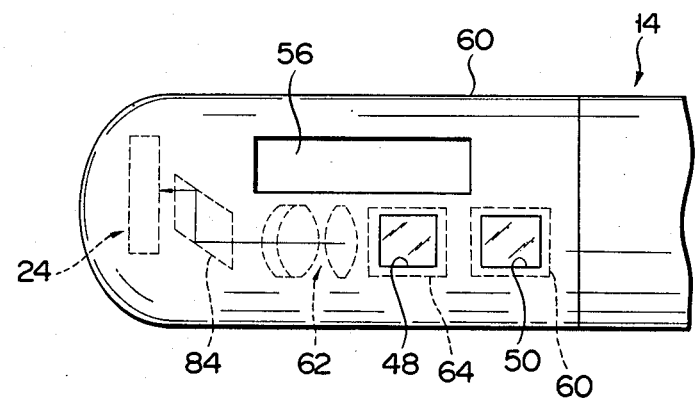
FIG. 6 is an enlarged side view of a distal end of an insertion section of an endoscope apparatus according to a third embodiment of the present invention.

According to a third embodiment shown in FIG. 6, a prism 84 having a rhombic shape is arranged as a third prism on an emitting side of an objective lens system 62. An optical image emitted from the lens system 62 is deflected twice by the prism 84 and thereafter becomes incident on a solid-state image sensor 24.

According to modifications shown in FIGS. 7 and 8, a portion of an end face of a package 68 of a solidstate image sensor 24 comprises an inclined surface 68a or a curved surface 68b. In these modifications, the end face of the package 68 can be brought close to the inside bottom of a cap 60 of an insertion section 14, so that the space in the distal end of the insertion section can be fully utilized.

FIG. 9 shows a fourth embodiment of the present invention. According to the fourth embodiment, a forward liquid supply switch 85 for supplying liquid to a body cavity is provided at a sub-operation section 28. A liquid supply unit 86 is arranged in a control unit 20. The liquid supply unit 86 includes a liquid tank 87, a pump 88 for pressurizing the liquid in the tank 87 and a supply pipe 89 for supplying pressurized liquid from the tank 87. An electromagnetic valve 90 is provided in the supply pipe 89. A liquid supply pipe 89a extends inside an endoscope 10 from the distal end of an insertion section 14 to a connector 18. When the connector 18 is connected to the control unit 20, the pipe 89a is connected to the pipe 89 and the switch 85 is electrically connected to the valve 90 and the pump 88 through a lead wire 91.

According to the fourth embodiment, when the switch 85 is operated, the pump 88 is operated and the valve 90 is opened. Then, the liquid in the tank 87 is supplied to the body cavity through the pipes 89 and 89a.

FIG. 10 shows a fifth embodiment of the present invention. According to the fifth embodiment, a circulation operation switch 92 is provided at a sub-operation section 28 for circulating a liquid or gas in a body cavity so as to prevent unnecessary expansion of, e.g., the stomach and so on. In an endoscope 10, a forward path tube 93 and a return path tube 94 extend from a distal end of an insertion section 14 to a connector 18. When the connector 18 is connected to a control unit 20, the pipe 93 communicates with a delivery port of a pump 95 in the control unit, and the pipe 94 communicates with an intake port of the pump 95 through a tank 96 arranged in the control unit. The operation switch 92 is electrically connected to the pump 96 through a lead wire 97.

According to the fifth embodiment described above, when the operation switch 92 is operated to operate the pump 95, air is supplied to the body cavity through the pipe 93. The pipe 94 is set at a negative pressure so that air and liquid in the body cavity are drawn by suction through the pipe 94. As a result, unnecessary expansion of the body cavity can be prevented.

FIG. 11 shows a sixth embodiment of the present invention. According to the sixth embodiment, a sub-operation section 28 having various operation switches is not formed midway along a universal cord 16 but detachably connected thereto. The section 28 is connected to a sub-control unit 20a incorporating a video processing circuit and so on through a cord 98. The unit 20a is connected to a control unit 20 through a connecting cord 99.

According to the sixth embodiment, when the section 28 is not needed, it can be disconnected from the universal cord 16, resulting in convenience.

FIG. 12 shows a seventh embodiment of the present invention. According to the seventh embodiment, a first sub-operation section 28 is provided on a universal cord 16 and a second sub-operation section 28a is detachably connected to the section 28. The section 28a is connected to a sub-control unit 20a through a cord 98 and the unit 20a is connected to a control unit 20 through a connecting cord 99. Operation switches which are used least frequently are provided to the section 28a.

According to the seventh embodiment, additional various operation switches can be provided in the vicinity of an operation section 12, improving operability of the endoscope apparatus. In addition, when the section 28a is not needed, it can be disconnected from the section 28.

FIG. 13 shows an eighth embodiment of the present invention. According to the eighth embodiment, a universal cord 16 is divided into two portions. A connecting plug 100 is connected to an extended end of a first portion 16a of the cord 16 extending from an operation section 12 of an endoscope 10. A connector 18 and a sub-operation section 28 to be connected to the connecting plug are connected to the ends, respectively, of a second portion 16b of the cord 16.

According to the eighth embodiment, the section 28 can be disconnected from the endoscope 10, facilitating handling and sterilization of the endoscope.

It must be noted that similar effects to those in the first embodiment can be obtained in the fourth to eighth embodiments described above.

What is claimed is:
1. An endoscope apparatus comprising:
a control unit having a light source; and
an endoscope, said endoscope including
an operation section,
an elongated insertion section extending from the operation section and having an observation window and an illumination window provided at the distal end thereof, said observation window being positioned nearer the distal end than the illumination window,
a universal cord extending from the operation section and detachably connected to the control unit, a light guide extending from the illumination window through the insertion section, operation section and universal cord for guiding light emitted from the light source and externally emitting the light from the illumination window, an objective lens system arranged in the insertion section and optically connected to the observation window for forming an optical image of light incident thereon through the observation window, and a solid-state image sensor arranged in the insertion section, positioned nearer the distal end of the insertion section than the end of the light guide at the illumination window side, and optically connected to the objective lens system for converting the optical image formed by the objective lens system to an electrical signal and transmitting the electrical signal to the control unit.

2. An apparatus according to claim 1, wherein said objective lens system includes a plurality of lenses, and at least one of said lenses is arranged such that its optical axis extends toward the distal end of the insertion section.

3. An apparatus according to claim 1, wherein said insertion section includes a flexible outer tube extending from the operation section, a columnar support fixed to an extended end of the outer tube and a cylindrical cap with its bottom fitted around an outer surface of the support, said support has a first mounting hole communicating with the illumination window and open at a proximal end side of the insertion section and a second mounting hole communicating with said observation window and open at a distal end side of the insertion section, said first and second mounting holes extend along an axial direction of the support, an extended end of said light guide is inserted and fixed in the first mounting hole, and said objective lens system is arranged in the second mounting hole.

4. An apparatus according to claim 3, wherein said solid-state image sensor is arranged between an end face of the support at a distal end side of the insertion section and the inside bottom of the cap and opposes an emitting side of the objective lens system.

5. An apparatus according to claim 4, wherein said endoscope includes adjusting means for adjusting focusing and inclination of the solid-state image sensor, and said adjusting means has a plurality of adjusting screws screwed from the outside into the cap for urging the solid-state image sensor against the support, and an elastic member arranged between the solid-state image sensor and an end face of the support at the distal end side of the insertion section.

6. An apparatus according to claim 1, wherein said control unit includes a video signal processing circuit for processing the electrical signal supplied from the solid-state image sensor, a monitor connected to the video signal processing circuit for displaying an image in accordance with a processed signal, and a video tape recorder connected to the video signal processing circuit for recording the image in accordance with the processed signal.

7. An apparatus according to claim 6, wherein said endoscope includes a sub-operation section provided on the universal cord near the operation section, said operation section has a plurality of operation switches, and said sub-operation section has an operation switch for operating the monitor and an operation switch for operating the video tape recorder.

8. An apparatus according to claim 1, wherein said endoscope includes a sub-operation section provided on the universal cord near the operation section, said operation section has a plurality of operation switches, and said sub-operation section has at least one additional operation switch.

9. An apparatus according to claim 8, wherein said sub-operation section is formed separately from the universal cord, detachably connected to the universal cord, and connected to the control unit.

10. An apparatus according to claim 8, wherein said universal cord is divided into a first portion extending from the operation section and a second portion, an end of which is connected to the control unit, said sub-operation section is provided on the other end of the second portion of the universal cord, and said endoscope includes a connecting plug connected to an extended end of the first portion of the universal cord and detachably connected to the sub-operation section.

11. An apparatus according to claim 1, wherein said operation section includes a plurality of operation switches, and said endoscope includes a first sub-operation section provided on the universal cord and having at least one additional operation switch, and a second sub-operation section detachably connected to the first sub-operation section and connected to the control unit and having at least one operation switch.

* * * * *